US012642953B2

(12) United States Patent (10) Patent No.: US 12,642,953 B2
Siess et al. (45) Date of Patent: *Jun. 2, 2026

(54) BLOOD PUMP WITH FILTER

(71) Applicant: Abiomed Europe GmbH, Aachen (DE)

(72) Inventors: Thorsten Siess, Aachen (DE); Walid Aboulhosn, Aachen (DE); Christoph Nix, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/372,173

(22) Filed: Sep. 25, 2023

(65) Prior Publication Data

US 2024/0123213 A1 Apr. 18, 2024

Related U.S. Application Data

(63) Continuation of application No. 17/113,654, filed on Dec. 7, 2020, now Pat. No. 11,833,278, which is a
(Continued)

(30) Foreign Application Priority Data

Mar. 23, 2016 (EP) ..................................... 16161944

(51) Int. Cl.
*A61M 60/135* (2021.01)
*A61M 60/13* (2021.01)
(Continued)

(52) U.S. Cl.
CPC .......... *A61M 60/135* (2021.01); *A61M 60/17* (2021.01); *A61M 60/216* (2021.01);
(Continued)

(58) Field of Classification Search
CPC .... A61M 1/10; A61M 1/1001; A61M 1/1005; A61M 1/101; A61M 1/1017;
(Continued)

(56) References Cited

U.S. PATENT DOCUMENTS 6,395,014 B1 5/2002 Macoviak et al.
7,241,257 B1 7/2007 Ainsworth et al.
(Continued)

FOREIGN PATENT DOCUMENTS

CN 103037929 A 4/2013
EP 2974695 A1 1/2016
(Continued)

OTHER PUBLICATIONS

ISR PCT/EP2017/056611, dated May 24, 2017 (4 pages).
(Continued)

*Primary Examiner* — Brian T Gedeon
(74) *Attorney, Agent, or Firm* — BOTOS CHURCHILL IP LAW LLP

(57) ABSTRACT

The invention relates to an intravascular blood pump. The blood pump comprises a pump section having a proximal portion with a blood flow inlet and a distal portion with a blood flow outlet and an impeller for causing blood to flow into the blood flow inlet and towards the blood flow outlet. The blood pump further comprises at least one filter connected to the proximal portion of the pump section and arranged with respect to the blood flow inlet so as to filter the blood before it enters the blood flow inlet. The filter may comprise an expandable mesh structure made of a shape-memory material.

20 Claims, 15 Drawing Sheets

Related U.S. Application Data continuation of application No. 16/087,480, filed as application No. PCT/EP2017/056611 on Mar. 21, 2017, now Pat. No. 10,898,629.

(51) Int. Cl.

| | |
|---|---|
| *A61M 60/17* | (2021.01) |
| *A61M 60/216* | (2021.01) |
| *A61M 60/237* | (2021.01) |
| *A61M 60/888* | (2021.01) |

(52) U.S. Cl.
CPC ... *A61M 60/888* (2021.01); *A61M 2205/0266* (2013.01); *A61M 2205/7545* (2013.01); *A61M 2205/7554* (2013.01); *A61M 2230/30* (2013.01)

(58) Field of Classification Search
CPC .............. A61M 1/1022; A61M 1/1024; A61M 1/1025; A61M 1/1037; A61M 1/1075; A61M 1/12; A61M 1/122; A61M 1/125; A61M 1/127; A61M 1/267; A61M 5/165; A61M 2005/1652; A61M 2005/1655; A61M 2005/1657
See application file for complete search history.

(56) References Cited

U.S. PATENT DOCUMENTS

| | | |
|---|---|---|
| 2003/0187322 A1 | 10/2003 | Siess |
| 2005/0154250 A1 | 7/2005 | Aboul-Hosn et al. |
| 2007/0208297 A1 | 9/2007 | Ainsworth et al. |
| 2008/0039786 A1 | 2/2008 | Epstein et al. |
| 2008/0086027 A1 | 4/2008 | Siess et al. |
| 2010/0185043 A1 | 7/2010 | Woodard et al. |
| 2013/0066140 A1 | 3/2013 | Mcbride et al. |
| 2014/0005674 A1 | 1/2014 | Angel et al. |
| 2014/0018912 A1 | 1/2014 | Delaloye et al. |
| 2020/0185043 A1 | 6/2020 | Sano et al. |

FOREIGN PATENT DOCUMENTS

| | | |
|---|---|---|
| GB | 2239675 A | 7/1991 |
| JP | 2009530041 A | 8/2009 |
| JP | 2010099215 A | 5/2010 |
| WO | 2007112033 A2 | 10/2007 |
| WO | 2015170733 A1 | 11/2015 |

OTHER PUBLICATIONS

Office Action for corresponding CN Application No. 201780018586.6 dated Jul. 3, 2020 with English Translation (33 pages).
Office Action from corresponding European Patent Application No. 17710983.2 dated May 4, 2023, (6 pp.).
Office Action issued in corresponding Japanese Patent Application No. 2022-010556 dated May 9, 2023 (7 pp.).
Office Action issued in corresponding Korean Patent Application No. 10-2018-7030548 dated Nov. 21, 2021, 16 pp.
Office Action from corresponding Japanese Patent Application No. 2024-115419 dated Nov. 4, 2025 (14 pp. ).

FIG 7
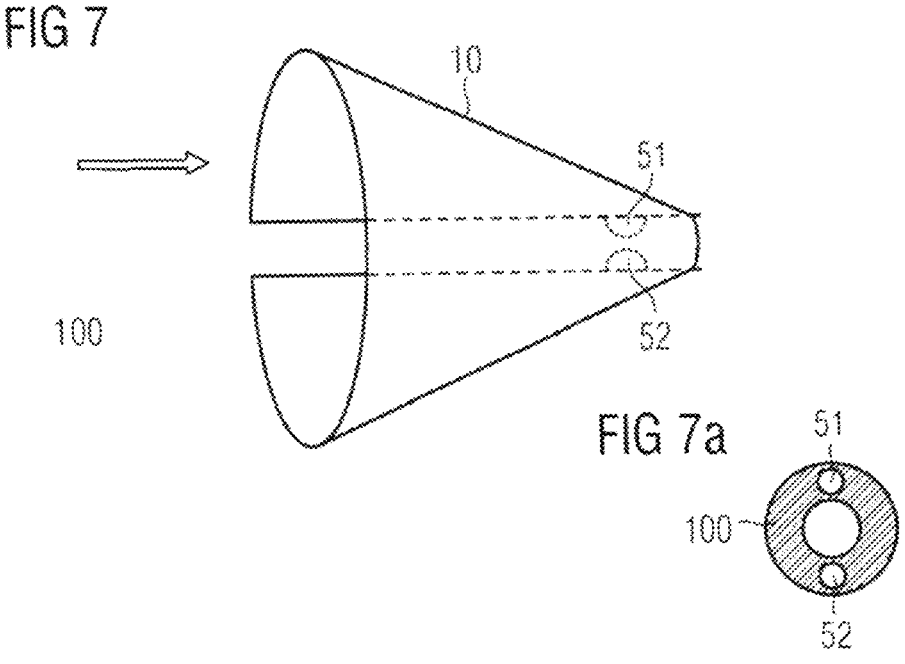
FIG 7a
FIG 8
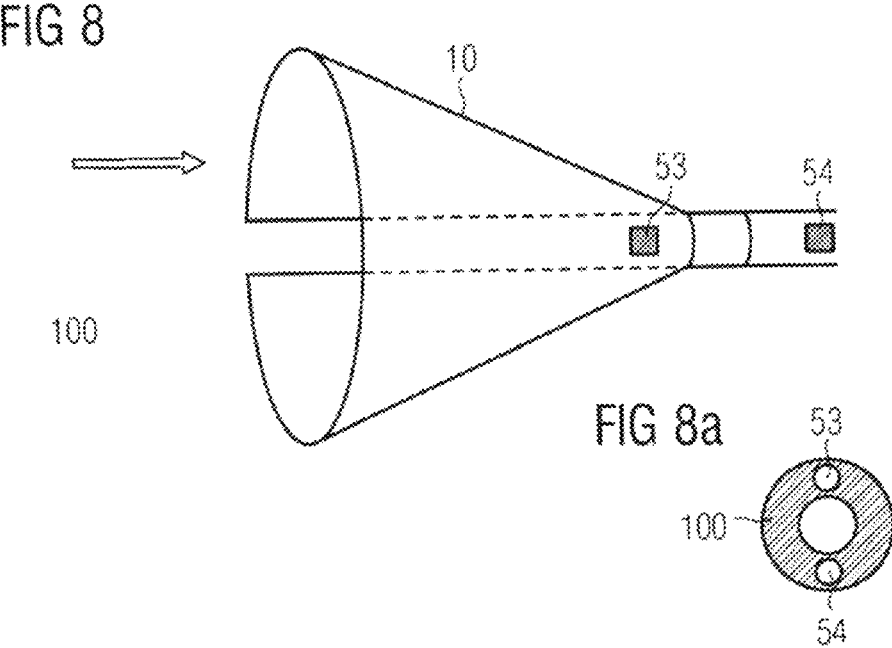
FIG 8a

BLOOD PUMP WITH FILTER

CROSS REFERENCE TO RELATED APPLICATIONS

This application is a continuation of U.S. patent application Ser. No. 17/113,654, filed Dec. 7, 2020, now allowed, which application is a continuation Ser. No. 16/087,480, filed Sep. 21, 2018, now U.S. Pat. No. 10,898,629, which application is a United States National Stage filing under 35 U.S.C. § 371 of International Application No. PCT/EP2017/ 056611, filed Mar. 21, 2017, which claims the benefit of European Patent Application No. 16161944.0, filed Mar. 23, 2016, the contents of all of which are incorporated by reference herein in their entirety. International Application No. PCT/EP2017/056611 was published under PCT Article 21(2) in English.

BACKGROUND

This invention relates to a blood pump, in particular an intravascular blood pump for percutaneous insertion into a patient's blood vessel, to support a blood flow in a patient's blood vessel. This invention particularly relates to a right ventricular blood pump to support a blood flow from the vena cava through the right ventricle into the pulmonary artery.

Intravascular blood pumps are inserted into a patient's vessel such as the aorta or vena cava and through a cardiac valve by means of a catheter and can also be referred to as catheter pumps. A blood pump typically comprises a pump section with a blood flow inlet and a blood flow outlet. In order to cause a blood flow from the blood flow inlet to the blood flow outlet, typically an impeller or rotor is rotatably supported within the pump casing about an axis of rotation for conveying blood. The blood pump may be driven by a motor included in the blood pump adjacent to the pump section or may alternatively be driven by a motor outside the patient's body, in which case the motor is connected to the impeller by a flexible drive shaft extending through the catheter.

A right ventricular blood pump is inserted through the inferior or superior vena cava through the right ventricle of a patient's heart into the pulmonary artery by means of a catheter. Typically, the blood flow inlet of the blood pump is placed inside the right atrium, vena cava or right ventricle, while the pump section extends through the tricuspid valve, the right ventricle and the pulmonary valve into the pulmonary artery.

Any blood clots or thrombi that occur may be conveyed from the vena cava to the pulmonary artery, which, however does not cause severe harm to the patient because the thrombi only end up in the pulmonary circulation. More importantly, blood clots tend to clog the blood pump and thus may cause failure of the blood pump, which has to be avoided. Filters are known that can be placed in the vena cava, such as balls of random Nitinol wires. However, handling of such filters adjunctively to the blood pump therapy may be cumbersome, e.g. their insertion and particularly removal would require an additional access point. Any access point carries a high risk of bleeding and infection. A correct alignment between blood pump and filter is necessary for performance and needs to be confirmed by means of visualization by echo or x-ray.

SUMMARY OF THE INVENTION

It is an object of the present invention to provide a blood pump that has a reduced risk of device failure or increased hemolysis caused by clogging by blood clots.

This object is achieved according to the present invention by a blood pump having the features of independent claim 1. Preferred embodiments and further developments of the invention are specified in the claims dependent thereon.

In one embodiment, the blood pump comprises at least one filter. The filter is associated with or connected to the proximal portion of the pump section and is arranged with respect to the blood flow inlet so as to filter the blood before it enters the blood flow inlet. This combination of a blood pump with at least one filter prevents blood clots from entering the blood pump or adhering to the inflow openings of the pump. This can prevent failure of the blood pump caused by clogging by blood clots. The free end of the blood pump is typically referred to as the distal end, whereas the catheter extends from the proximal end. In this embodiment, the blood thus flows in a direction from proximal to distal.

Preferably, the filter comprises a mesh structure, in particular a regular mesh structure. A mesh structure may comprise a plurality of apertures that are defined and separated by struts. The apertures may have any size and shape, such as circular, round, elongate, rectangular or polygonal. A regular structure comprises structures of equal and/or repeating dimensions, such as size, shape or distances. Providing a regular mesh structure makes it possible to provide a filter with predetermined filter properties, e.g. blood clots of a predetermined size can be retained by the filter, while smaller blood clots can pass through the filter, which may be advantageous compared to a randomly shaped filter. The apertures of the filter may have an average size of about 20 μm to about 240 μm, preferably about 40 μm to about 120 μm.

In one embodiment, the filter is expandable from a compressed configuration to an expanded configuration. In particular, the filter may be expandable at least in a radial direction to abut against an inner wall of a blood vessel in which the filter is to be arranged during operation of the blood pump. The filter can be inserted into the blood vessel in the compressed configuration, e.g. inside an introducer sheath. Upon expansion, the filter may abut against the inner vessel wall to close the vessel and to avoid unfiltered blood bypassing the filter. An expandable device may also facilitate removal if it can be compressed or collapsed.

At least a portion of the filter, or the entire filter, may comprise or may be made of a shape-memory material, such as a shape-memory alloy, preferably Nitinol. Plastic shape-memory material may also be used. A shape-memory material is preferred when the filter is to exhibit expansion properties. After being compressed, the filter returns to its expanded configuration, e.g. under the influence of temperature.

In one embodiment, the filter is attached to an elongate extension member extending from the proximal portion of the pump section such that the filter is proximally spaced from the pump section. The extension member may be part of the pump section, in particular the proximal portion thereof. The extension member preferably comprises a catheter. In particular, the extension member may be formed by a catheter.

The filter may be fixedly attached to the extension member. Alternatively, it may be releasably attached to the extension member so as to be displaceable along the length of the extension member. The displaceable filter can be moved along the extension member to adjust its position, e.g. in the inferior vena cava, or may be removed from the patient by sliding it along the extension member. The filter can, thus, be removed for instance if it is clogged and has to be cleaned or exchanged, without having to remove the blood pump from the patient.

In one embodiment, the filter has a distal end and a proximal end, wherein the distal end of the filter is attached to the extension member and the proximal end is an open end in order to form an inlet opening for the blood flow into the filter. In particular, the filter may taper from the proximal end towards the distal end and may form a conical shape or funnel shape. In other words, a cross-sectional dimension of the filter may decrease in the direction of the blood flow. While the distal end of the filter may be closed by being attached to the expansion member, the proximal end may form the inlet opening of the filter and may abut against the inner wall of the blood vessel.

As explained above, the filter preferably comprises a mesh structure, in particular a regular mesh structure, defining a plurality of apertures. Preferably, the apertures at the distal end have a smaller cross-sectional dimension than the apertures at the proximal end. This is particularly advantageous in the aforementioned embodiment, in which the distal end of the filter is attached to the extension member and the proximal end forms an open end such that the filter has a funnel shape. Blood clots will accumulate in the tip, i.e. the distal end, of the filter, while more proximal regions of the filter are still open for blood to pass through. The blood clots in the tip can be removed e.g. by suction and/or lysing, as described in more detailed hereinafter.

The filter may comprise a retaining device coupled to the proximal end of the filter and extending in a proximal direction, such that actuation of the retaining device causes the filter to collapse from an expanded configuration to a collapsed configuration. In one embodiment, the retaining device may comprise at least one filament, preferably a plurality of filaments, such as three, four, five or six, attached to the open proximal end of the filter, such that pulling the at least one filament causes the filter to collapse. The filaments may be regularly spaced about the circumference of the filter. The provision of a retaining device facilitates removal of the filter. For instance, the filter can be collapsed and can be retracted into an introducer sheath for removal.

In one embodiment, as an alternative or in addition to the features described with reference to the previous embodiment, the proximal end of the filter may be attached to the blood pump proximally with respect to the blood flow inlet. In particular, the filter may extend at least partially or completely over the blood flow inlet. Furthermore, the distal end of the filter may also be attached to the blood pump distally with respect to the blood flow inlet such that the filter encloses the blood flow inlet. In other words, rather than being disposed proximally with respect to the blood flow inlet, the filter may directly cover or enclose the blood flow inlet. As in the previous embodiment, the filter may comprise a mesh structure, may be expandable and may comprise a shape-memory material, such as Nitinol. In this embodiment, the filter may be for instance ball-shaped or may be formed of two cones that are connected at their largest diameter. Of course, other shapes may be suitable.

In one embodiment, the blood pump may comprise at least two filters that are arranged in series. The filters may be designed identically or differently, in particular in accordance with any of the above described embodiments. For instance, a coarse filter followed by a fine filter may be provided, i.e. filters having a mesh structure with apertures may be provided, with the mesh structure of a distal filter having smaller apertures compared to a proximal filter.

At least one of the filters may be fixedly attached to the blood pump and at least another one of the filters may be releasably attached to the extension member so as to be displaceable along the length of the extension member as described above. Preferably, the fixedly attached filter is disposed distally with respect to the releasably attached filter. Alternatively, each of the filters may be releasably attached to the blood pump, in particular an extension member such as a catheter, so as to be displaceable along the length of the extension member. It may also be possible that each of the filters is fixedly attached.

Rather than being arranged in series, at least two filters may be provided that are arranged to be independently placed in different blood vessels that lead to the blood flow inlet during operation. For example, one of the blood vessels is a patient's inferior vena cava and another one of the blood vessels is the patient's superior vena cava. The at least two filters may be provided as at least one first filter that is connected to the blood pump and at least one additional filter that is separate from the blood pump and may be attached to and inserted with a separate catheter. Preferably, the at least one additional filter is arranged to be placed in the superior vena cava. In another embodiment, the additional filter may be arranged to be placed in the inferior vena cava, while the filter attached to the blood pump is arranged to be placed in the superior vena cava. The at least one additional filter may be formed like any of the aforementioned filters.

In one embodiment, the blood pump may comprise at least one pressure sensor for measuring the blood pressure. Preferably, the blood pump comprises at least two pressure sensors for measuring the blood pressure, with at least one of the pressure sensors being located downstream of the at least one filter and at least another one of the pressure sensors located upstream of the at least one filter. This allows measuring a pressure difference caused by the at least one filter and provides an indicator of whether the filter is clogged and has to be removed or cleaned.

The blood pump may comprise at least one suction port located in the filter, in particular in a downstream end portion of the filter, that permits blood clots to be removed from the filter through the suction port. Blood clots can be sucked continuously, at predetermined intervals or only when needed, which can be determined e.g. by means of the aforementioned pressure sensors. Alternatively or in addition, the blood pump may comprise at least one lysing port located in the filter, in particular in a downstream end portion of the filter, in order to supply a lysing agent to the filter to lyse blood clots accumulated in the filter. The lysed blood clots may either be sucked through the suction port or pass through the filter if they are sufficiently small. The suction port and lysing port may facilitate cleaning of the filter and may help to increase the time of operation of the blood pump without removal of the filter.

In one embodiment, alternatively or in combination with the aforementioned embodiments, the filter may be formed in the blood flow inlet. Further alternatively or in addition, the apertures of the filter may define the blood flow inlet. That means that the apertures of the filter may be designed, e.g. with respect to size and shape, to form the blood flow inlet, such that no separate filter is necessary. Vice versa it can be said that the blood flow inlet is designed to form the apertures of the filter. In other words, the filter may be formed by the blood flow inlet itself, where the apertures are small enough to prevent blood clots from entering the pump section. The filter is preferably formed integrally with the pump section, but may also be formed as one or more inserts. The filter may have a regular mesh structure as described above, for example elongate slot-like apertures separated by struts. It will be appreciated that the apertures may have any other size and shape, regular or irregular, suitable for preventing blood clots to enter the blood pump. For instance, the apertures may be formed directly in the pump section, e.g. by punching or laser cutting. It will be appreciated that said filter which is formed by the blood flow inlet may be combined with at least one additional filter. In other words, the blood pump may comprise at least two filters, in particular a first filter proximal of the blood flow inlet and a second filter which apertures form the blood flow inlet. The apertures may be circular, oval, square, polygonal or otherwise shaped as desired, and may have a width of about 40 μm to about 120 μm.

The blood pump with the filter as described above preferably is an intravascular pump, i.e. a catheter pump. In particular, the blood pump may be a right ventricular blood pump, configured for insertion into the right ventricle of a patient's heart through the vena cava, preferably through the inferior vena cava. Preferably, at least one of the at least one filter is sized and configured for being placed in the inferior vena cava, and the pump section is configured to extend through the right ventricle of a patient's heart such that the blood flow inlet is disposed in the inferior vena cava or right atrium and the blood flow outlet is disposed in the pulmonary artery. The filter prevents blood clots from entering the pulmonary circulation and prevents blood clots from clogging the blood pump.

In one embodiment, there may be provided for a blood pump a filter that is configured to be connected to a proximal portion of a pump section of the blood pump so as to be arranged with respect to a blood flow inlet of the blood pump to filter a blood flow before entering the blood flow inlet. The filter preferably comprises a regular mesh structure. Further preferably, the filter is formed like any of the aforementioned filters.

A kit may be provided that comprises a blood pump and a filter that can be attached to the blood pump. As mentioned before, the filter may be displaceable along the length of the catheter so as to allow removing the filter, e.g. for replacing the filter or cleaning the filter, without removing the blood pump from the patient. The kit may comprise a plurality of different filters, e.g. with respect to aperture size, so that an appropriate filter can be chosen depending on the application or depending on the patient's needs. The filter may be placed over the blood pump either during manufacturing of the blood pump, i.e. the filter and the blood pump may be preassembled, or the filter may be pushed over the blood pump just prior to insertion of the blood pump into the patient. The filter may be formed like any of the aforementioned filters.

In one embodiment the filter may be formed as a sleeve, in particular as cylindrical sleeve or sheath, that can be placed over the blood flow inlet. For instance, the filter may simply be advanced along the length of the catheter until it is placed over the blood flow inlet. The filter may be press fit onto the pump section. An inner diameter of the filter may substantially correspond to an outer diameter of the pump section. A distal end of the filter may be tapered to facilitate insertion and to avoid a step at the distal end of the filter.

Alternatively, a shoulder may be provided on the pump section, which serves as a stop for the filter when the filter is advanced in a distal direction onto the pump section. Further alternatively, a circumferential recess may be provided around the pump section in which the blood flow inlet may be disposed. The filter may then snap fit into the recess when it is advanced over the pump section. In order to facilitate adding and removing the filter to and from the blood pump, the filter may be slit along its length to allow placement over the catheter from the side, i.e. in a direction transverse to a central axis of the blood pump. Preferably, the filter is elastic or made of a shape memory material such that the slit closes once the filter is placed over the catheter. The filter may be a metallic member, e.g. a metallic sleeve, that can be placed over the blood flow inlet. The apertures of the filter may be formed e.g. by laser cutting, punching or the like.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings:

FIG. 7 schematically shows a filter according to another embodiment.

FIG. 7a shows a schematic cross-sectional view of the catheter of the filter of FIG. 7.

FIG. 8 schematically shows a filter according to another embodiment.

FIG. 8a shows a schematic cross-sectional view of the catheter of the filter of FIG. 8.

DETAILED DESCRIPTION

Figure 1:
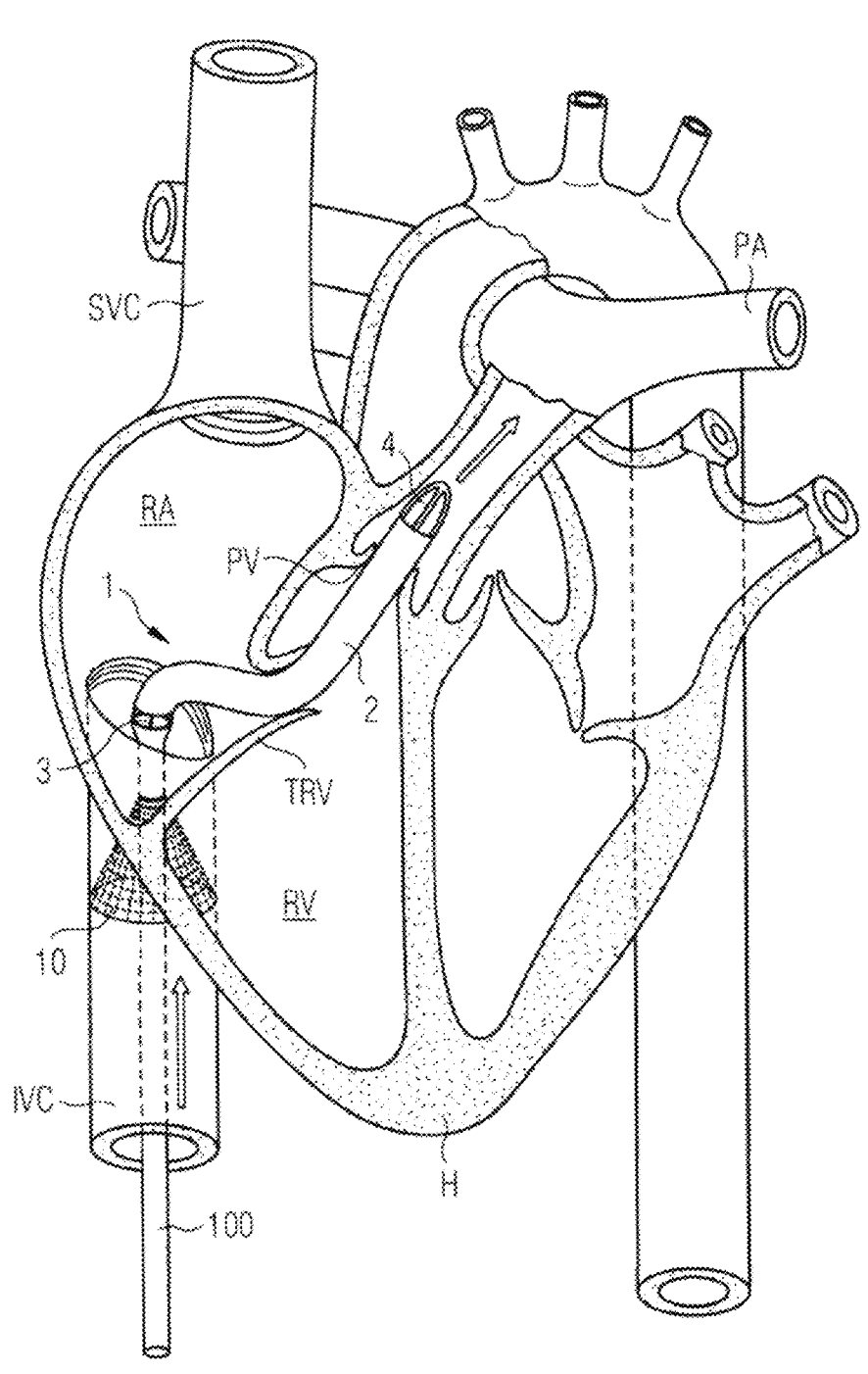
FIG. 1 shows a patient's heart with a blood pump inserted through the right ventricle.

In FIG. 1 is illustrated a blood pump 1 inserted into a patient's heart H. More specifically, the blood pump 1 is connected to a catheter 100 by means of which the blood pump 1 is inserted into the right ventricle RV of the patient's heart H via the inferior vena cava IVC. In a different approach, the catheter may be inserted through the superior vena cava SVC. During its operation, the blood pump 1 is placed through the tricuspid valve TRV and the pulmonary valve PV. The blood pump 1 comprises a pump section 2 having a blood flow inlet 3 placed in the right atrium RA and a blood flow outlet 4 placed in the pulmonary artery PA. An impeller (not shown) is provided to cause the blood to flow into the blood flow inlet 3 towards and out of the blood flow outlet 4 (see arrows). A filter 10 is connected to the blood pump 1, more specifically attached to the catheter 100, and placed in the inferior vena cava IVC and abuts against the inner wall of the inferior vena cava IVC. Thus, the blood flow is filtered before it enters the blood flow inlet 3 and blood clots are prevented from entering the blood pump 1. The blood pump 1 according to this embodiment is designed as a right ventricular blood pump.

7

Figure 2:
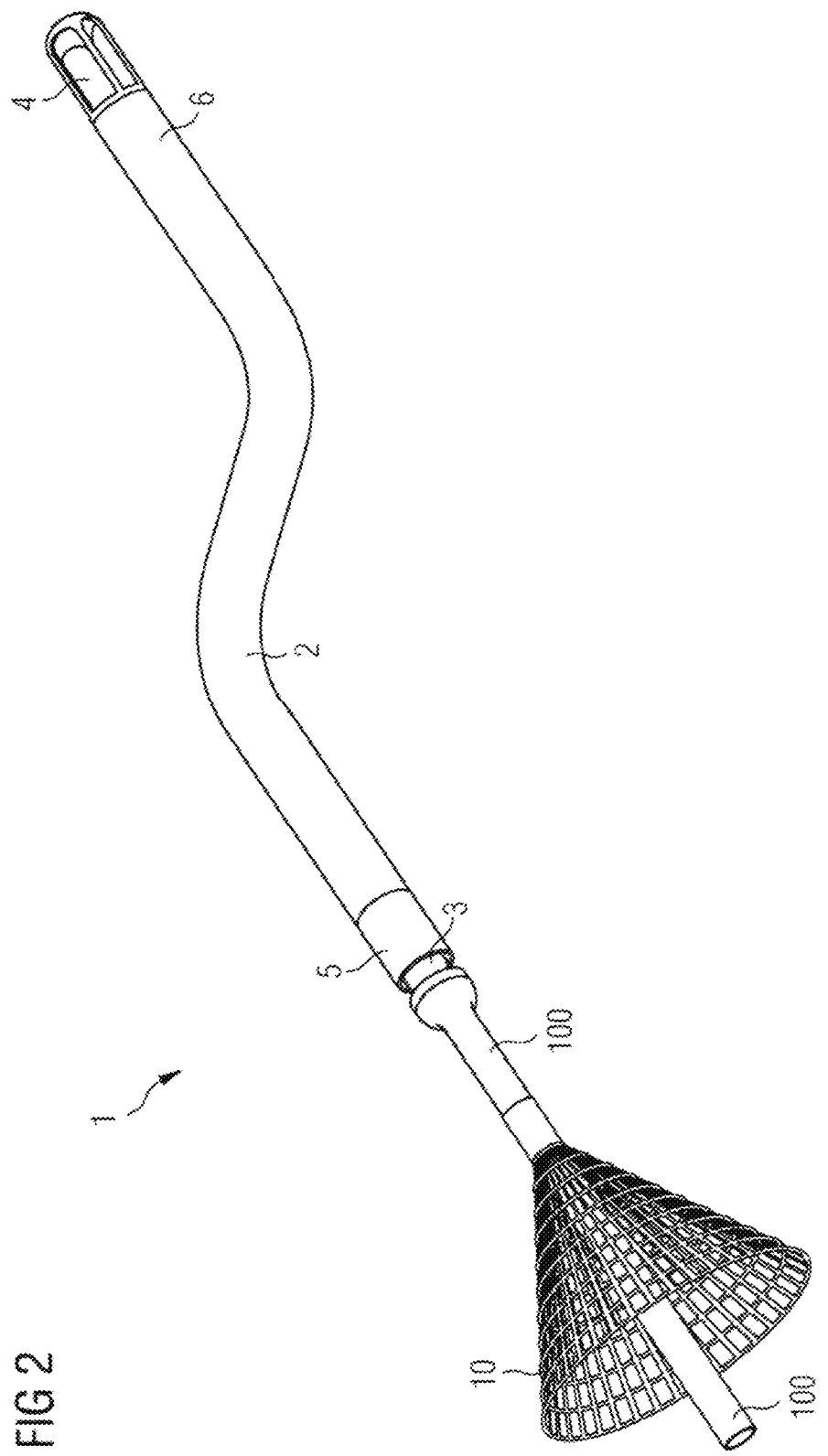
FIG. 2 shows the blood pump of FIG. 1 in more detail.

With reference to FIG. 2, the blood pump 1 shown in FIG. 1 is illustrated in more detail. The curved pump section 2 has a proximal portion 5 with the blood flow inlet 3 and a distal portion 6 with the blood flow outlet 4. In this embodiment, the catheter 100 extends from the proximal portion 5 of the pump section 2. The pump section 2 has a specific curvature which helps to prevent the blood pump 1 from backing out of the patient's heart H. The blood flow inlet 3 and the blood flow outlet 4 are formed as circumferential openings in this embodiment. It will be appreciated that other shapes, sizes or positions may be suitable for the blood flow inlet 3 and the blood flow outlet 4, possibly depending on the application. The filter 10 is located upstream of the blood flow inlet 3, i.e. proximally with respect to the blood flow inlet 3, so as to filter the blood before it enters the blood flow inlet 3. More specifically, the filter 10 is mounted on the catheter 100 in an end portion of the catheter 100 adjacent to the pump section 2.

Figure 3:
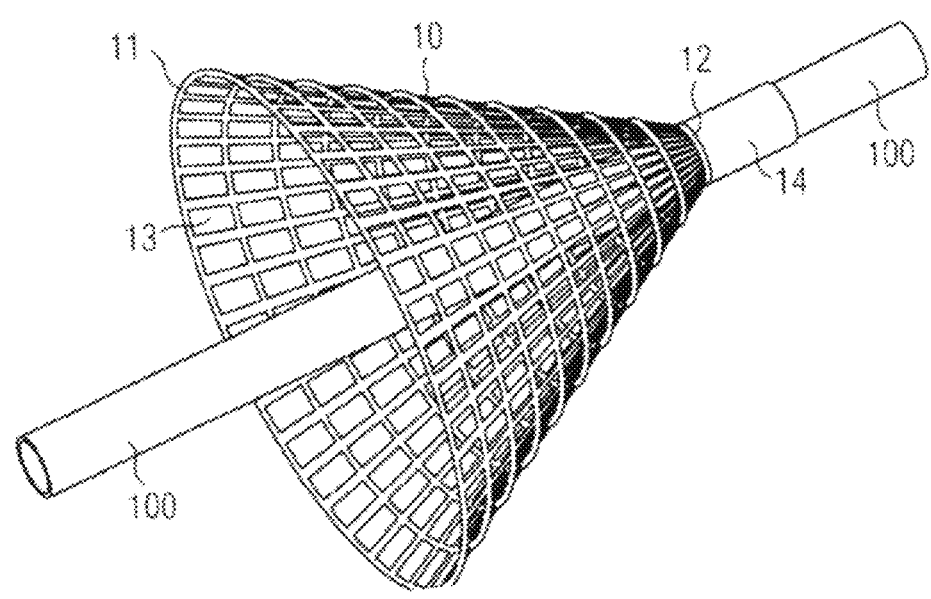
FIG. 3 shows the filter of the blood pump of FIG. 1.

The filter 10 is illustrated in more detail in FIG. 3. The filter 10 is attached to the catheter 100 with its distal end 12. Therefore, the distal end 12 of the filter 10 can be regarded as being closed. A bushing 14, sleeve or the like may be used to attach the distal end 12 to the catheter 100. The filter 10 may either be fixedly attached to the catheter 100 or may be movable along the length of the catheter 100, e.g. to allow adjustment of the position of the filter 10 and/or to allow removal of the filter 10. The proximal end 11 of the filter 10 is open such that blood can enter the filter 10. In the illustrated embodiment, the filter 10 tapers from the proximal end 11 to the distal end 12 and has a conical shape. It will be appreciated that the filter 10 may have another suitable shape that provides an attachment at the distal end and an open proximal end.

The filter 10 has a regular mesh structure that defines a plurality of apertures 13. In this embodiment, the apertures 13 are rectangular and get narrower in a direction towards the distal end 12. This is caused by the conical shape of the filter 10 since the number of apertures 13 in a circumferential direction is constant along the length of the filter 10. Alternatively or in addition, the mesh structure may change towards the distal end 12 to provide smaller apertures towards the distal end 12, e.g. by adding additional radial and/or axial struts, by varying the shape of the apertures, etc.

The filter 10 is expandable from a compressed configuration to an expanded configuration. In the compressed configuration, the blood pump 1 with the filter 10 can be delivered through an introducer sheath (not shown) to the patient's heart H. After the blood pump 1 has been put in place, the filter 10 can be expanded. This allows the filter 10 to abut against the inner wall of a blood vessel, such as the inferior vena cava IVC as shown in FIG. 1. In order to provide the desired expansion properties, the filter 10 preferably is made of Nitinol or other suitable shape-memory material.

Figure 4:
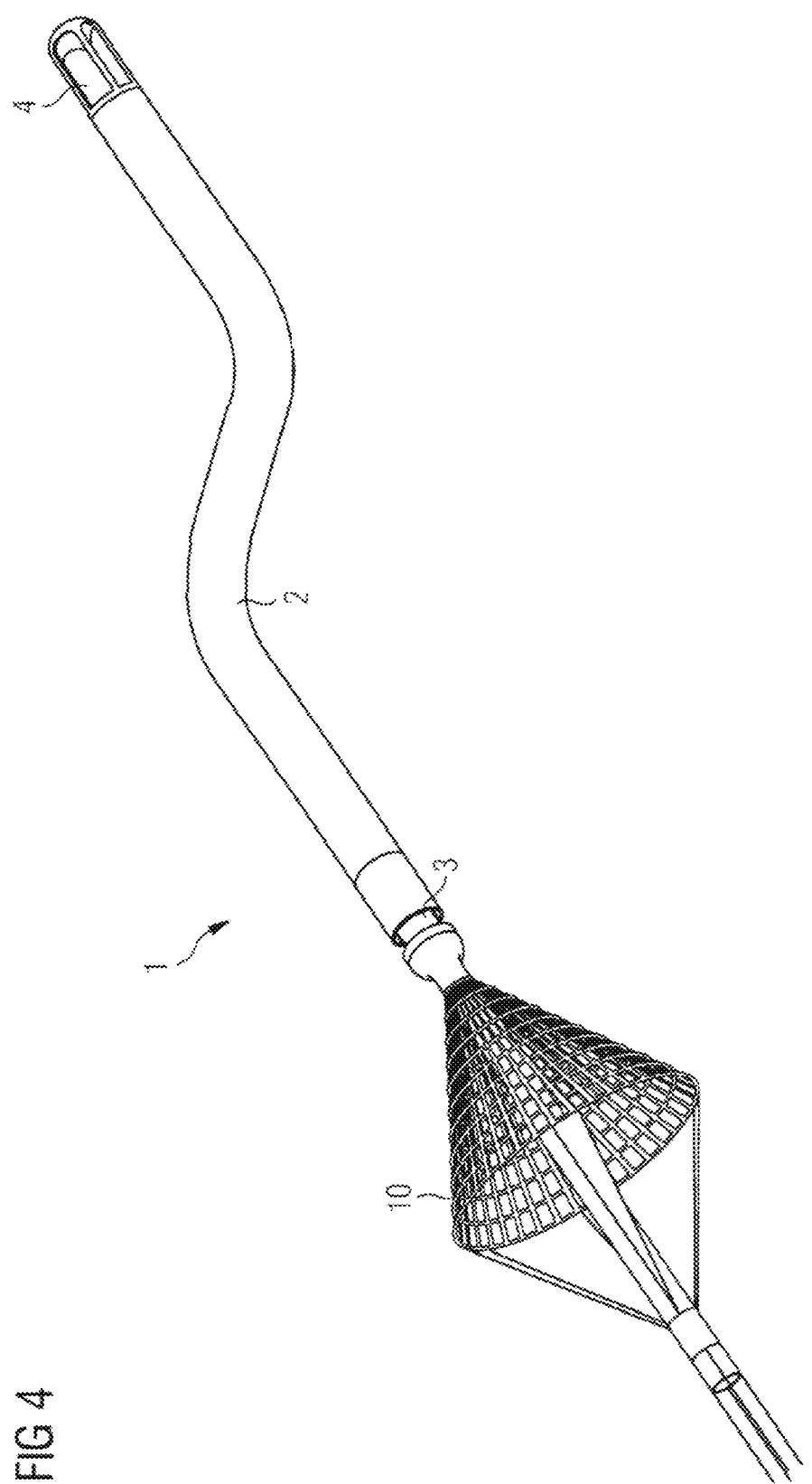
FIG. 4 shows another embodiment of a blood pump.
Figure 5:
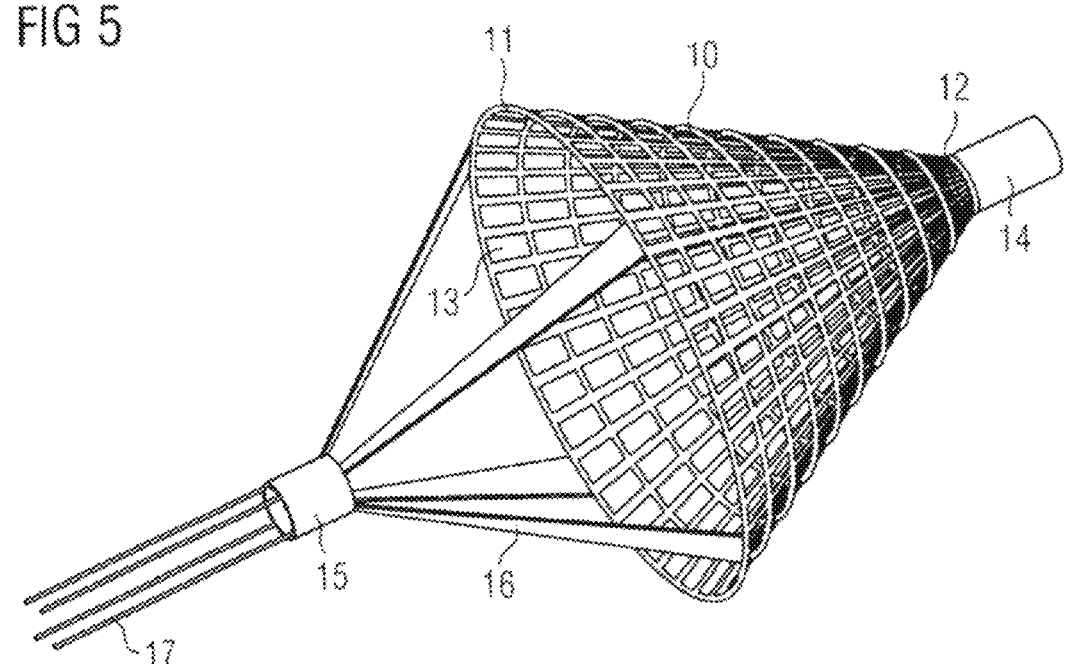
FIG. 5 shows the filter of the blood pump of FIG. 4.

FIGS. 4 and 5 show another embodiment of a blood pump 1 with a filter 10 that is substantially identical to the previous embodiment. Like reference numerals refer to like parts. In this embodiment, the filter 10 has a retaining device that facilitates removal of the filter 10. The retaining device includes a plurality of filaments 16 or bands that are connected to the open proximal end 11 of the filter 10. In the illustrated embodiment, four filaments 16 are provided that are equally spaced about the circumference of the filter 10. It will be appreciated that more or fewer filaments may be provided. The filaments are preferably formed integrally with the filter. They may end in a bushing 15 that can slide along the catheter 100 (catheter not shown in FIG. 5). Further filaments 17, threads, wires or the like are provided that can be manipulated, in particular pulled, by an operating person to collapse the filter 10. The filter 10 may then be retracted into an introducer sheath (not shown). The collapsed configuration may be identical to the initial compressed configuration or may provide a larger diameter that is nonetheless sufficiently small to enable the filter 10 to be removed. Removal of the filter may be necessary e.g. for cleaning or simply if the blood pump 1 is to be finally removed from the patient.

Figure 6:
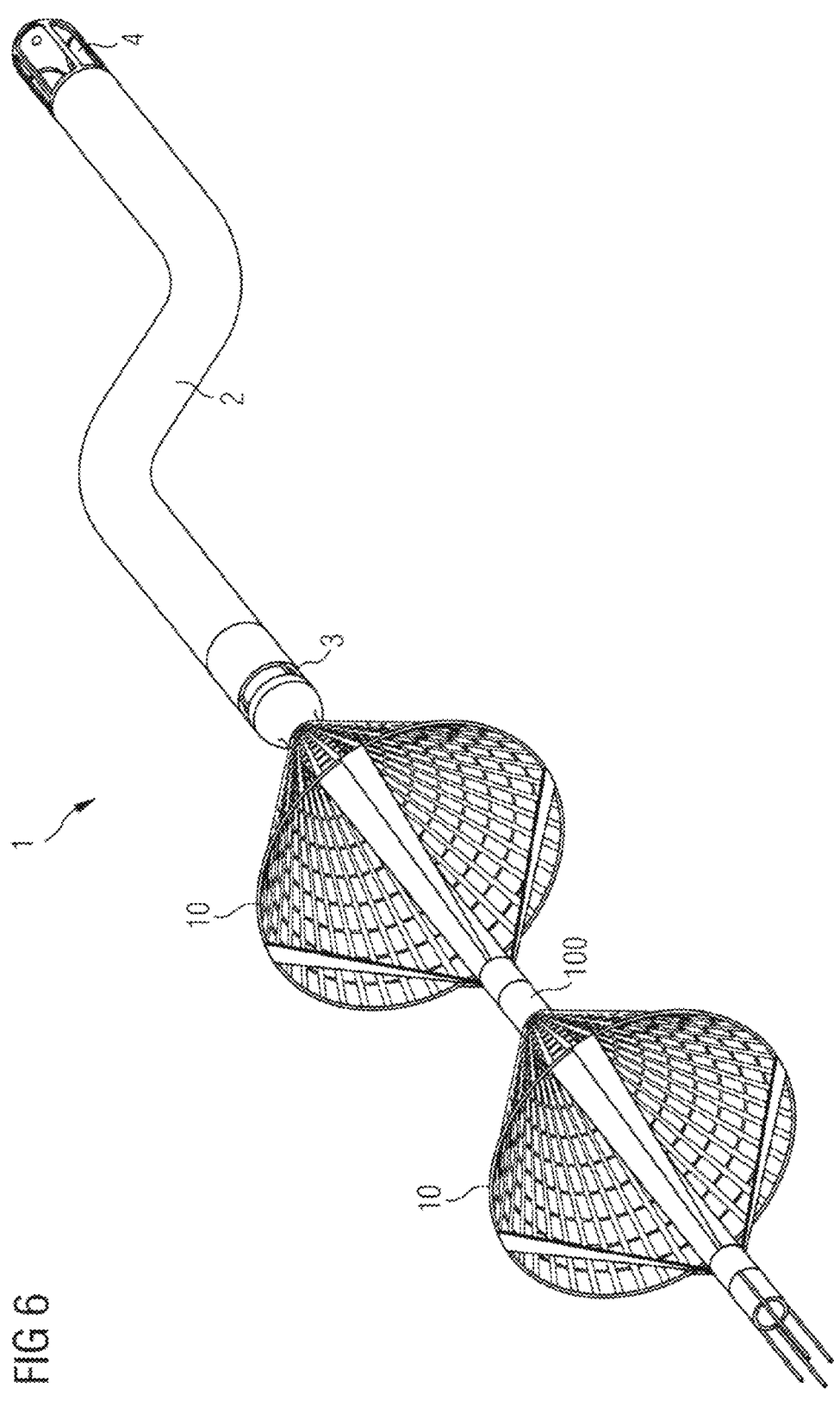
FIG. 6 shows another embodiment of a blood pump having two filters.

Referring now to FIG. 6, another embodiment of a blood pump 1 is illustrated which is substantially similar to the previous embodiment. In contrast to the previous embodiments, more than one filter is provided. In particular, two filters 10 are provided that are arranged in series on the catheter 100. In the embodiment shown in FIG. 6, both filters 10 are formed like the filter of FIGS. 4 and 5. Alternatively, both filters 10 may be formed like the filter of FIGS. 2 and 3, or the filters 10 may be formed differently. Both filters 10 may be fixedly attached to the catheter 100 or both may be movable. In one embodiment, only one of the filters 10, preferably the proximal one, is movable or releasably attached to the catheter, while the other one, preferably the distal one, is fixed.

FIGS. 7 and 8 show further embodiments of a filter 10. The mesh structure is not shown for clarity purposes. The filter 10 shown in FIG. 7 includes a suction port 51 and a lysing port 52 near the distal end of the filter 10. Blood clots that accumulate in the downstream tip, i.e. the distal end, of the filter 10 can be removed by being sucked through the suction port 51. Alternatively or in addition, the blood clots may be lysed by a lysing agent that is supplied to the filter 10 through the lysing port 52. As shown in the schematic cross-sectional view of FIG. 7a, the suction port 51 and lysing port 52 may be connected to respective lines that extend through the catheter 100. It will be appreciated that only one of the ports 51, 52 may be provided.

The filter 10 shown in FIG. 8 includes two pressure sensors 53, 54. The pressure sensor 53 is located inside the filter 10, whereas the pressure sensor 54 is located downstream, i.e. distally, with respect to the filter 10. This arrangement of two pressure sensors 53, 54 allows measuring a pressure difference caused by the filter 10. If the pressure difference exceeds a predetermined threshold, this can indicate a blockage of the filter 10. As shown in the schematic cross-sectional view of FIG. 8a, the pressure sensors 53, 54 may be connected to respective lines that extend through the catheter 100. It will be appreciated that the features of the embodiments of FIGS. 7 and 8 may be combined in a single embodiment.

Figure 9:
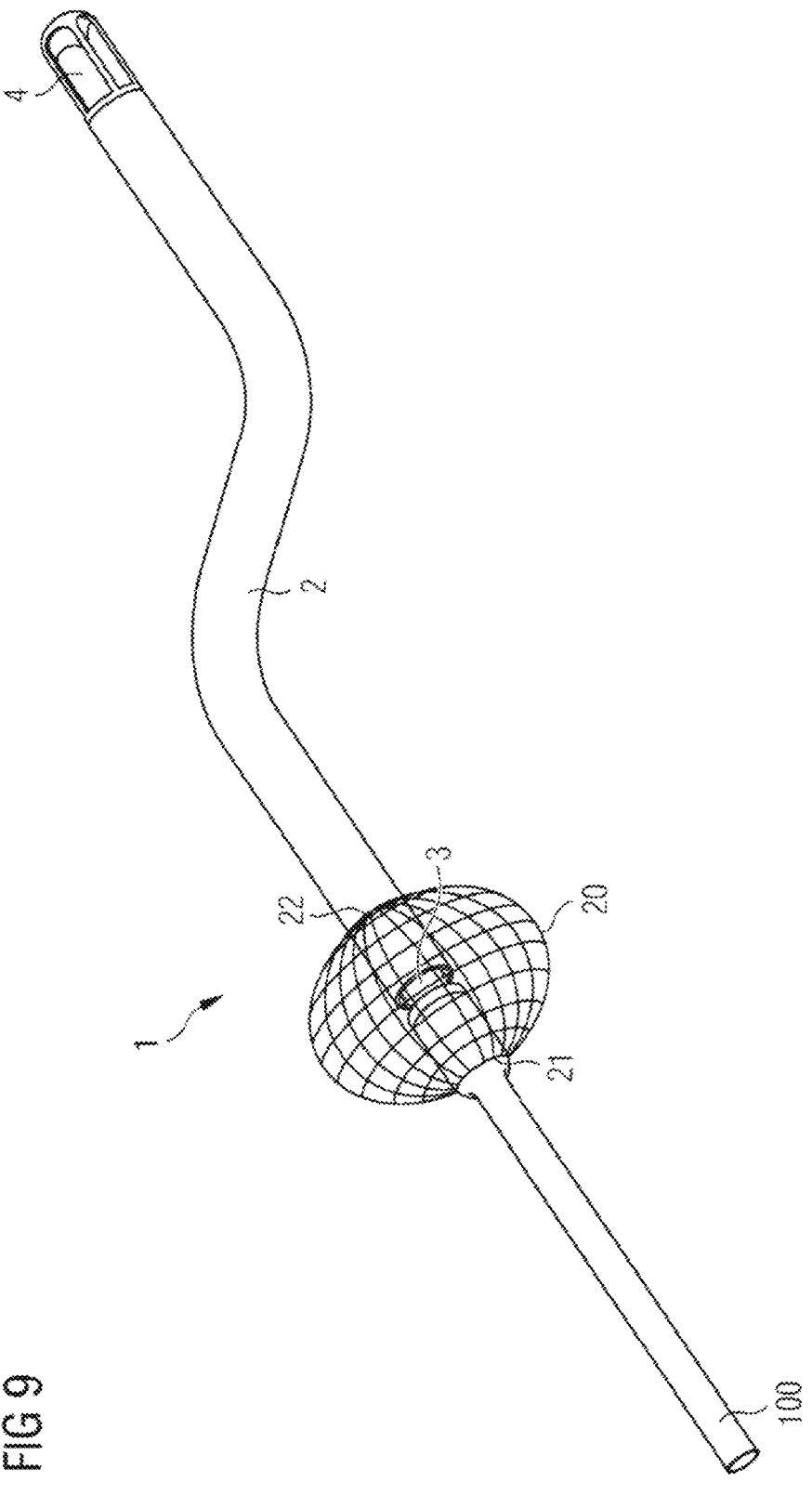
FIG. 9 shows another embodiment of a blood pump.

Another embodiment of a blood pump 1 is illustrated in FIG. 9. Rather than a tapered filter 10 that is disposed proximally with respect to the pump section 2, a filter 20 is provided that encloses the blood flow inlet 3. A proximal end 21 of the filter 20 is attached to the pump section 2 proximally with respect to the blood flow inlet 3 and a distal end 22 of the filter 20 is attached to the pump section 2 distally with respect to the blood flow inlet 3. In particular, the filter 20 may be formed like a cage and preferably has a mesh structure. The cage is preferably expandable and may be made of Nitinol or other shape-memory material as described above with respect to the filter 10. The filter 20 may be provided alternatively or in addition to any of the aforementioned filters 10.

Figure 10:
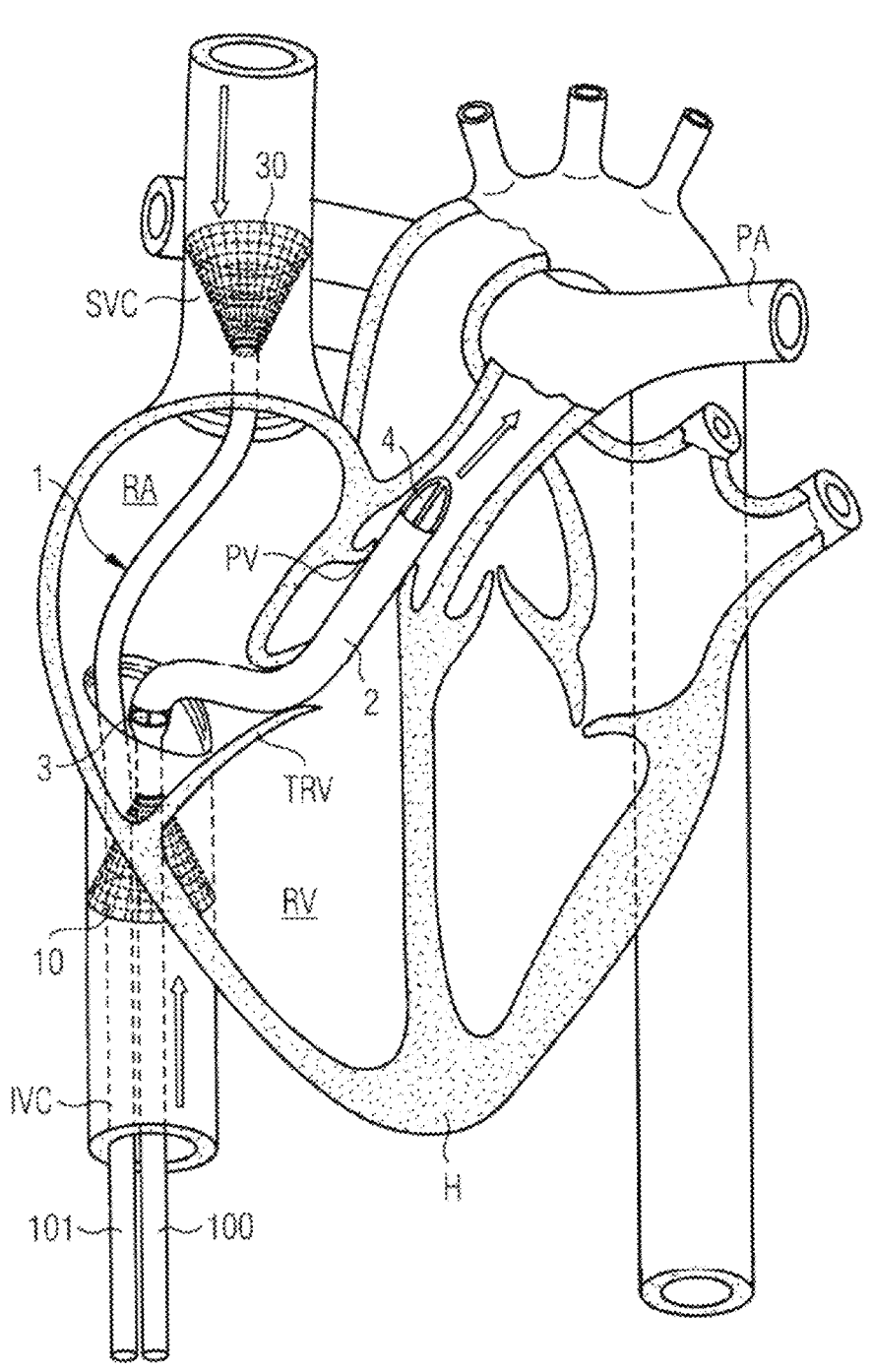
FIG. 10 shows a patient's heart with a blood pump inserted through the right ventricle and an additional filter.

With reference to FIG. 10, a system including a blood pump 1 with a filter 10 and an additional filter 30 is illustrated. The blood pump 1 may be formed in accordance with any one of the aforementioned embodiments. The illustrated blood pump 1 is the blood pump of FIG. 1. The additional filter 30 is provided for also filtering blood that comes from the superior vena cava SVC. The filter 30 is attached to an additional catheter 101 that is inserted through the inferior vena cava IVC which allows using the same vascular access that is used for the blood pump 1. The catheter 101 extends past the filter 10. Alternatively, an additional access can be used and the catheter 101 along with the filter 30 can be inserted though the superior vena cava SVC, which could be advantageous for securely holding the filter 30 in place. Of course, in the latter case the filter 30 will be attached to the catheter 101 in the opposite direction. The filter 30 is designed like any of the aforementioned filters 10. More than one, such as two or three, filters 30 may be provided on the catheter 101. The filter 30 may be identical to or different from the filter 10 of the blood pump 1. It will be appreciated that the arrangement can be vice versa, i.e. the catheter 100 with the blood pump 1 is inserted through the superior vena cava SVC, while the additional filter 30 is placed in the inferior vena cava IVC.

Figure 11A:
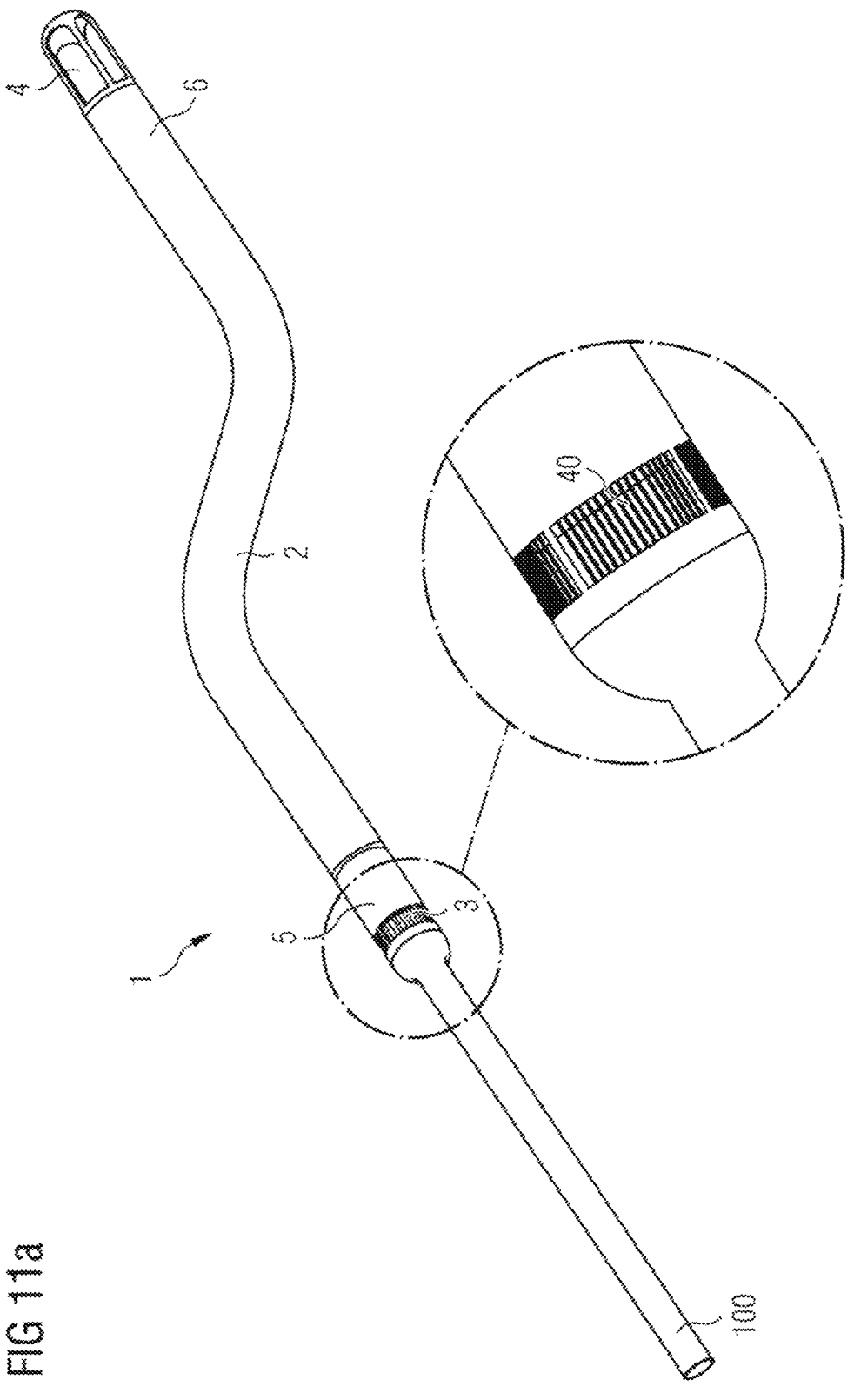
FIGS. 11a and 11b show yet another embodiments of a blood pump.
Figure 11B:
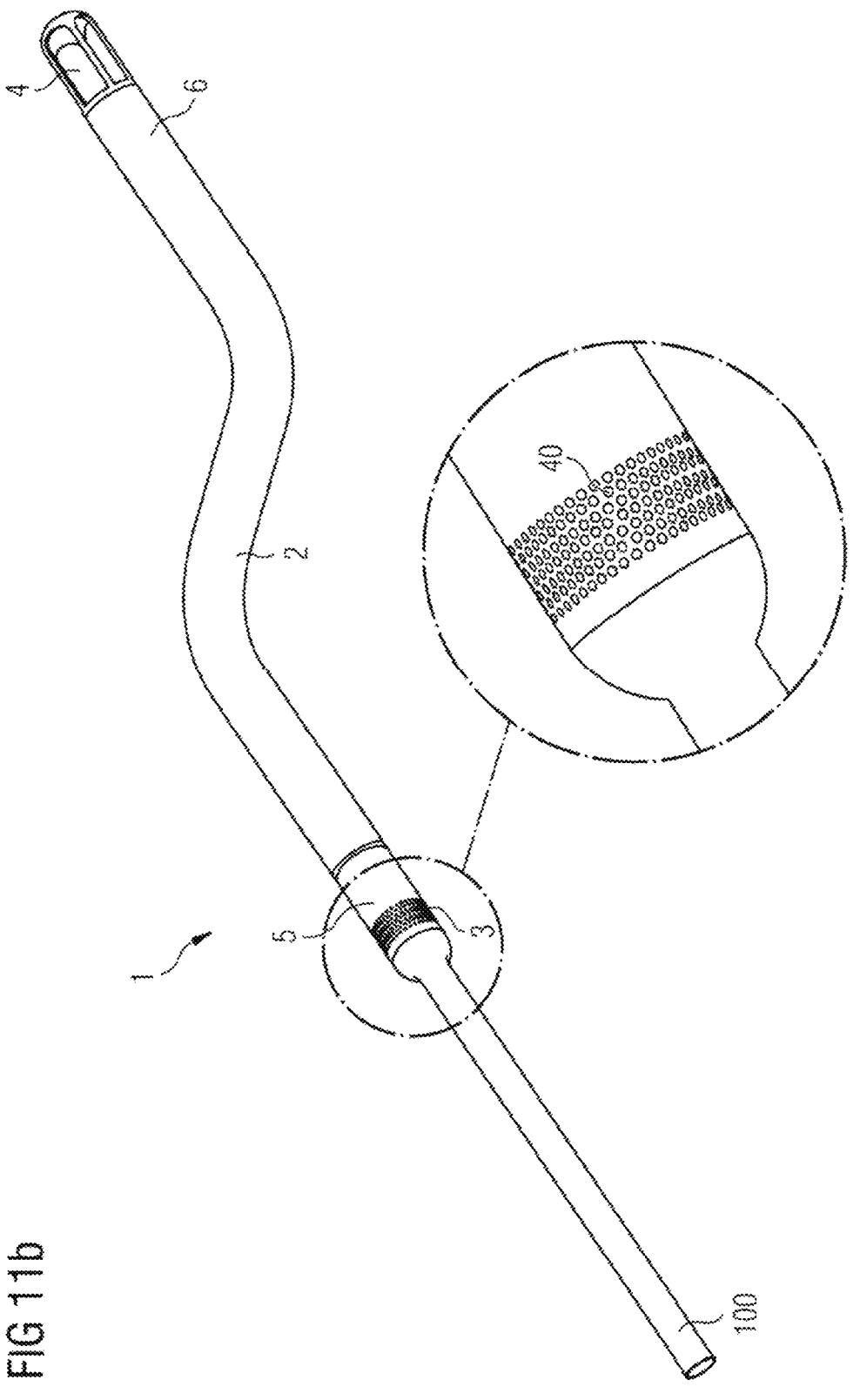

Yet another embodiment of a blood pump 1 is illustrated in FIGS. 11a and 11b. In contrast to the aforementioned embodiments, the blood pump 1 of this embodiment has a filter 40 that is integrated directly in the blood flow inlet 3. The filter 40 is integrally formed with the pump section 2, which provides an easy-to-manufacture structure. It is also possible to provide the filter 40 as an insert for the blood flow inlet 3. The apertures of the filter 40 may be elongate slots that extend in the longitudinal direction and that are separated by struts as shown in FIG. 11a. However, other shapes may be suitable for the apertures, such as circumferential slots or rectangular or circular openings as shown in FIG. 11b. The width of the slots or openings is chosen to prevent clots from entering the pump section 2. In other words, the blood flow inlet 3 is formed by the apertures of the filter 40. It will be appreciated that a blood pump that includes the filter 40 can further include any one of the aforementioned filters 10, 20 and 30.

Figure 12A:
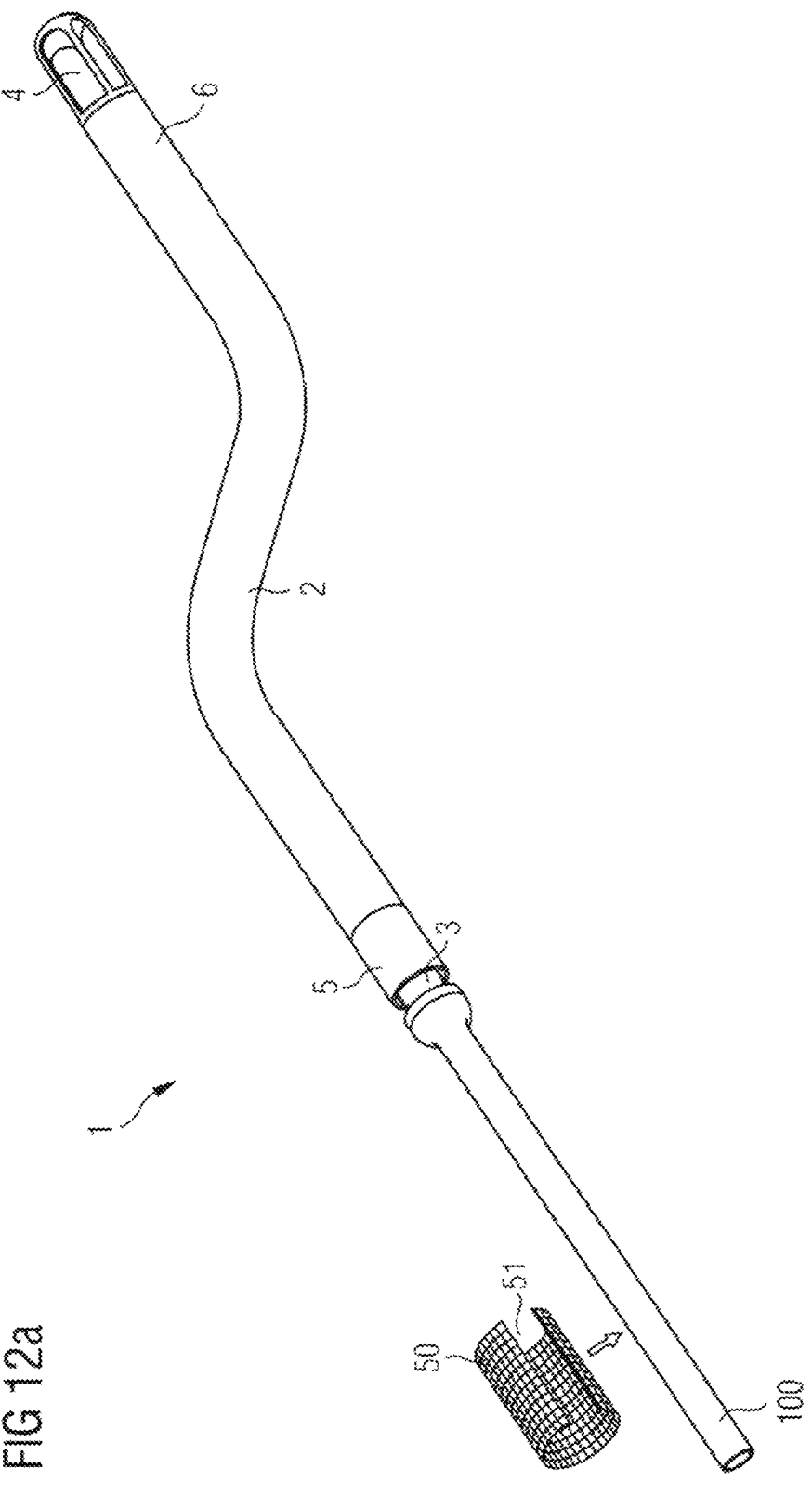
FIGS. 12a to 12c show assembly steps of a filter into a blood pump.
Figure 12B:
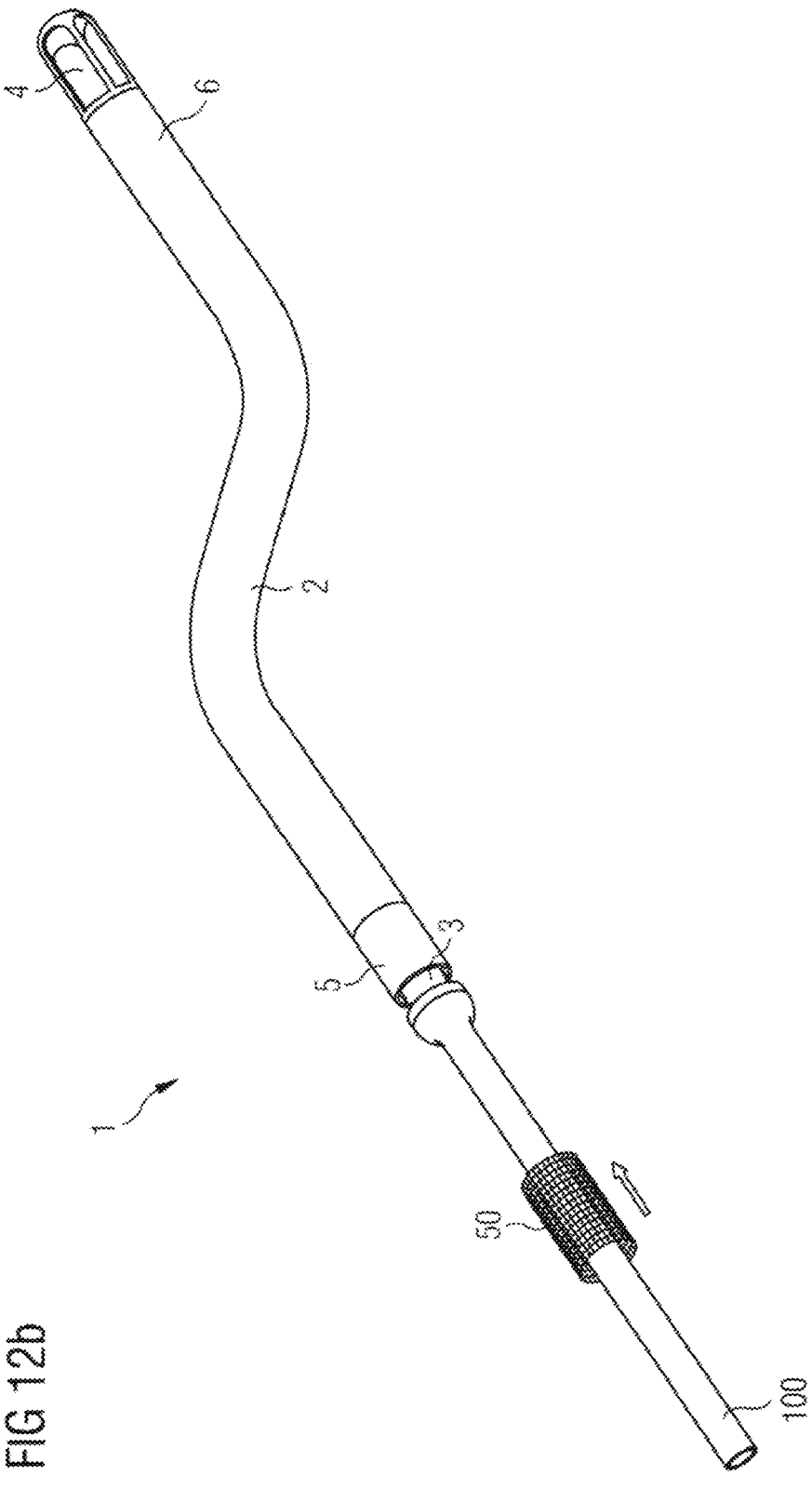
Figure 12C:
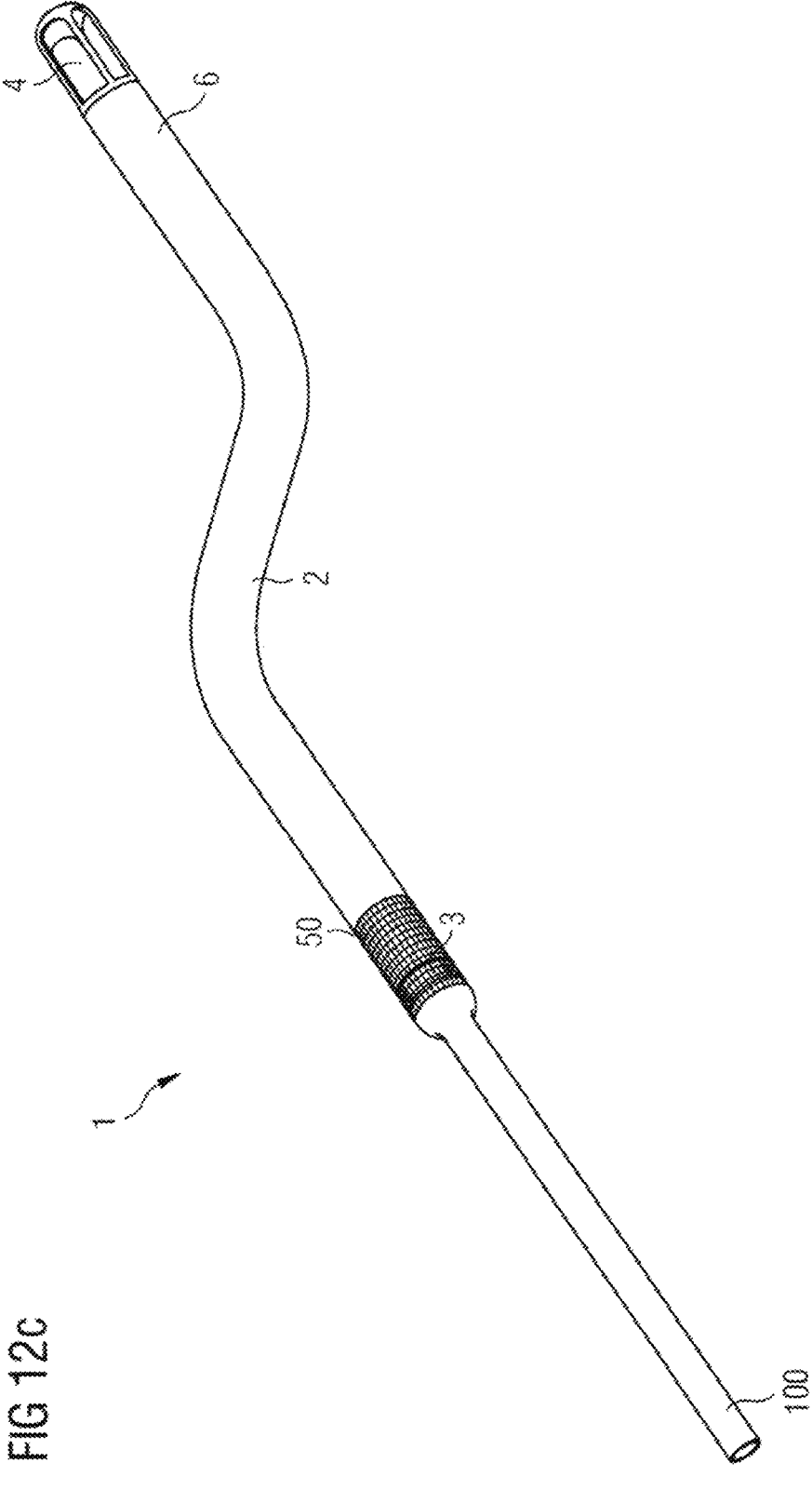

Referring to FIGS. 12a to 12c, a kit including a blood pump 1 and a filter 50 is shown. As illustrated in FIG. 12a, a filter 50 may be provided separately from the blood pump 1 and may have a longitudinal slit 51 to allow the filter 50 to be put onto the catheter 100 in a lateral direction, i.e. from the side as indicated by the arrow in FIG. 12a. The filter 50 is made of an elastic material or shape memory material, such as nitinol, in order to allow bending the filter into an open configuration and close it once placed over the catheter 100. The filter 50 may then be advanced in a distal direction towards the pump section 2 of the blood pump 1 as shown in FIG. 12b and indicated by the arrow. In the final position as shown in FIG. 12c, the filter 50 covers the blood flow inlet 3 of the blood pump 1 to prevent clots from entering the pump section 2, which helps to avoid failure of the blood pump by clogging. Referring again to FIG. 12b, it will be appreciated that the filter 50 may not have a slot but may be a circumferentially closed sleeve that is advanced onto the catheter 100 from the proximal end of the catheter 100 towards the pump section 2. For instance, the filter 50 may be preassembled on the catheter 100. The filter 50 may have any suitable mesh structure and aperture configuration as described above.

Figure 13A:
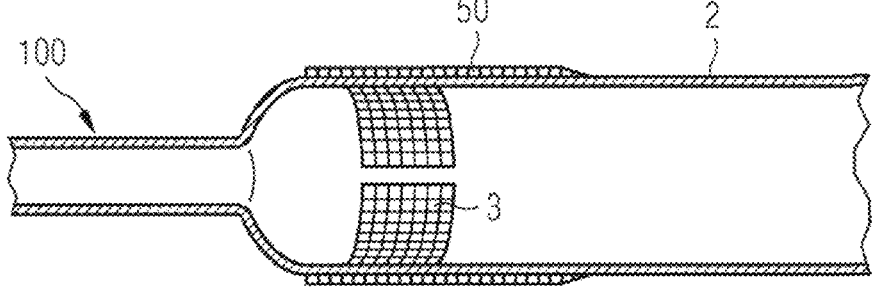
FIGS. 13a to 13c show different embodiments of placing a filter on the blood pump.
Figure 13B:
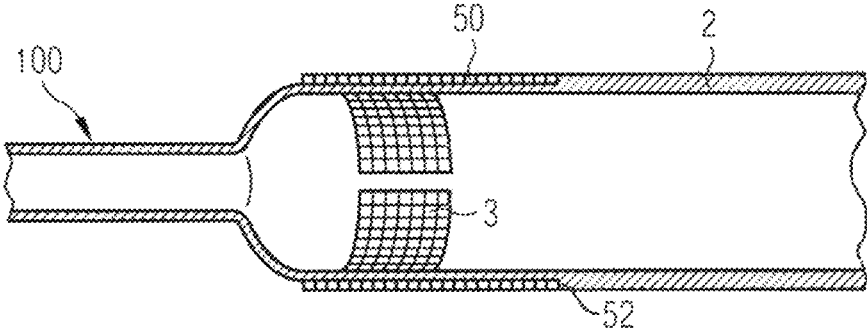
Figure 13C:
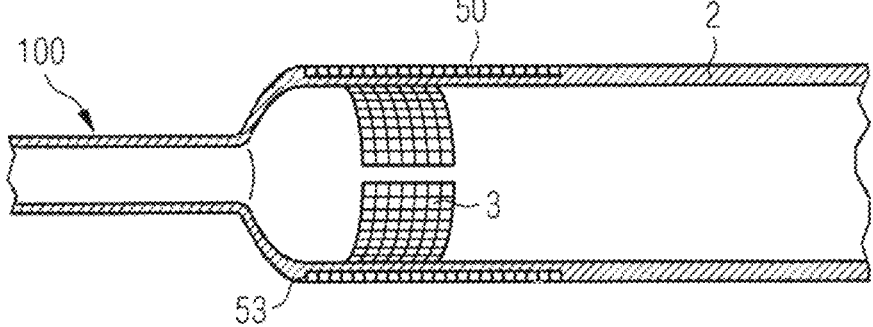

The filter 50 may simply be press fit onto the pump section 2 as shown in FIG. 13a, wherein the inner diameter of the filter substantially corresponds to or is slightly smaller than the outer diameter of the pump section 2. Since the blood pump 1 is preferably a right ventricular assist device, the increased diameter of the blood pump 1 is not as crucial as in other applications. In order to facilitate insertion, the filter 50 may be tapered at its distal end. As shown in FIG. 13b, the pump section 2 may have a step or shoulder 52. The filter 50 may abut the shoulder 52, which acts as a stop for the filter 50. Preferably, the outer circumference of the filter 50 and the pump section 2 are flush. Alternatively, as shown in FIG. 13c, a circumferential recess 53 may be provided which is sized and shaped to receive the filter 50 in a snap fit manner. The blood flow inlet 3 is disposed in the recess 53 such that the filter 50 covers the blood flow inlet 3 when received in the recess 53.

A kit with a separate filter 50 that is assembled onto a blood pump 1 provides a modular and flexible system. For instance, a surgeon can choose an appropriate filter just before inserting the blood pump based on the patient's needs. Alternatively, the kit provides an easy way of manufacturing a blood pump with a filter because the filter is formed like a sleeve that can simply be pushed onto the pump section.

The invention claimed is:

1. An intravascular blood pump for percutaneous insertion into a patient's blood vessel, the intravascular blood pump comprising:
  a pump section comprising:
  a proximal portion having a blood flow inlet;
  a distal portion having a blood flow outlet;
  an impeller for causing blood to flow into the blood flow inlet and towards the blood flow outlet; and
  a recessed portion formed in an exterior of the pump section, the recessed portion configured to receive a removable filter for filtering blood entering the blood flow inlet, wherein the blood flow inlet is formed in the recessed portion.

2. The intravascular blood pump of claim 1, wherein the recessed portion extends circumferentially around the exterior of the pump section.

3. The intravascular blood pump of claim 1, wherein the recessed portion is sized and shaped to receive the filter in a snap fit.

4. The intravascular blood pump of claim 1, wherein the recessed portion is configured such that, when the filter is received in the recessed portion, an exterior of the filter and the exterior of the pump section adjacent to the recessed portion are flush.

5. The intravascular blood pump of claim 1, wherein the recessed portion has a first circumference and a portion of the pump section adjacent to the recessed portion has a second circumference, wherein the first circumference is smaller than the second circumference.

6. The intravascular blood pump of claim 1, wherein the recessed portion is configured to receive a filter sleeve.

7. The intravascular blood pump of claim 1, further comprising at least one pressure sensor for measuring blood pressure.

8. The intravascular blood pump of claim 1, wherein the intravascular blood pump is a catheter pump.

9. The intravascular blood pump of claim 1, wherein the intravascular blood pump is a right ventricular blood pump configured for insertion into the right ventricle of a patient's heart through the inferior vena cava.

10. The intravascular blood pump of claim 1, wherein the pump section is configured to extend through the right ventricle of a patient's heart such that the blood flow inlet is disposed in the inferior vena cava and the blood flow outlet is disposed in the pulmonary artery.

11. An intravascular blood pump for percutaneous insertion into a patient's blood vessel, the intravascular blood pump comprising:

a pump section comprising:

a proximal portion having a blood flow inlet;

a distal portion having a blood flow outlet;

an impeller for causing blood to flow into the blood flow inlet and towards the blood flow outlet; and a shoulder formed on the pump section such that, when a filter for filtering blood entering the blood flow inlet is received on the pump section and covers the blood flow inlet, the filter abuts the shoulder.

12. The intravascular blood pump of claim 11, wherein the shoulder is configured to prevent distal advancement of the filter when the filter abuts the shoulder.

13. The intravascular blood pump of claim 11, wherein the shoulder extends circumferentially around an exterior of the pump section.

14. The intravascular blood pump of claim 11, wherein the pump section comprises a first portion having a first circumference and a second portion having a second circumference, wherein the first circumference is smaller than the second circumference.

15. The intravascular blood pump of claim 14, wherein the blood flow inlet is formed in the first portion of the pump section.

16. The intravascular blood pump of claim 14, wherein first portion of the pump section is configured to receive the filter and the first portion is configured such that, when the filter is received on the first portion, an exterior of the filter and an exterior of the second portion of the pump section are flush.

17. The intravascular blood pump of claim 11, further comprising at least one pressure sensor for measuring blood pressure.

18. The intravascular blood pump of claim 11, wherein the intravascular blood pump is a catheter pump.

19. The intravascular blood pump of claim 11, wherein the intravascular blood pump is a right ventricular blood pump, configured for insertion into the right ventricle of a patient's heart through the inferior vena cava.

20. The intravascular blood pump of claim 11, wherein the pump section is configured to extend through the right ventricle of a patient's heart such that the blood flow inlet is disposed in the inferior vena cava and the blood flow outlet is disposed in the pulmonary artery.

\* \* \* \* \*